United States Patent [19]

Brigati

[11] Patent Number: 4,731,335
[45] Date of Patent: Mar. 15, 1988

[54] METHOD FOR TREATING THIN SAMPLES ON A SURFACE EMPLOYING CAPILLARY FLOW

[75] Inventor: David J. Brigati, Dauphin, Pa.

[73] Assignee: Fisher Scientific Company, Pittsburgh, Pa.

[21] Appl. No.: 775,864

[22] Filed: Sep. 13, 1985

[51] Int. Cl.[4] ............................................. G01N 1/12
[52] U.S. Cl. .............................. 436/180; 73/864.72; 118/421; 422/100; 436/63; 427/2; 427/4
[58] Field of Search ............ 73/863.23, 864.72, 864.02, 73/61.1 C; 350/534–536; 427/2, 4; 436/63, 162, 178–180; 422/100, 102; 118/421

[56] References Cited

U.S. PATENT DOCUMENTS

| | | | |
|---|---|---|---|
| 2,415,480 | 2/1947 | Gassert | 350/535 |
| 2,863,319 | 12/1958 | McLin | 73/864.72 |
| 3,837,795 | 9/1974 | Becker et al. | 427/2 |
| 4,116,637 | 9/1978 | Kitahara | 73/864.02 |
| 4,199,613 | 4/1980 | Johnson | 427/4 |
| 4,308,028 | 12/1981 | Elkins | 23/230 B |
| 4,320,157 | 3/1982 | Hagens | 427/4 |
| 4,323,536 | 4/1982 | Columbus | 422/100 |
| 4,377,641 | 3/1983 | Dee et al. | 436/132 |
| 4,447,140 | 5/1984 | Campbell et al. | 350/534 |
| 4,549,952 | 10/1985 | Columbus | 422/100 |

FOREIGN PATENT DOCUMENTS

| | | |
|---|---|---|
| 10456 | 4/1980 | European Pat. Off. |
| 14797 | 9/1980 | European Pat. Off. |
| 1244844 | 9/1971 | United Kingdom |
| 2008270 | 5/1979 | United Kingdom |
| 2152700 | 8/1985 | United Kingdom |

Primary Examiner—Michael S. Marcus
Attorney, Agent, or Firm—Alan M. Doernberg

[57] ABSTRACT

Liquid is applied to a thin sample on a first surface (e.g., a specimen on a microscope slide) by maintaining a second surface parallel to the first to provide a gap therebetween and contacting an edge of the gap with a discrete aliquot of liquid. The liquid can migrate by capillary action into contact with the thin sample, preferably upward from horizontally extending linear edges of the surfaces. Liquid can also be removed by contacting the gap edges with absorbent material. Also disclosed are apparatus for holding a plurality of such surfaces in a vertically extending array and apparatus for holding a plurality of liquid droplets beneath the array. One apparatus can be moved relative to the other to contact the lower gap edges with droplets.

36 Claims, 16 Drawing Figures

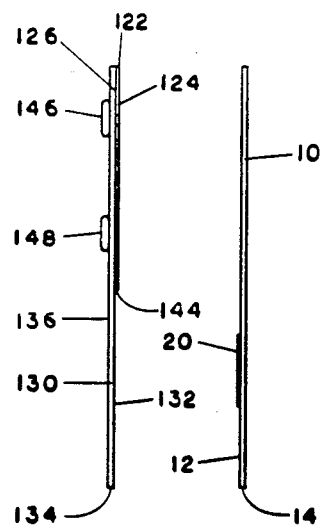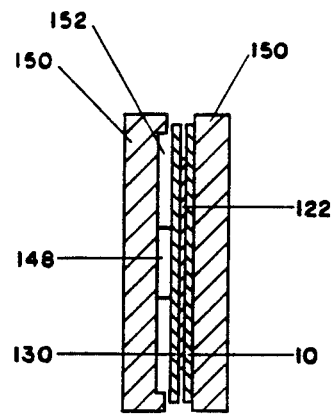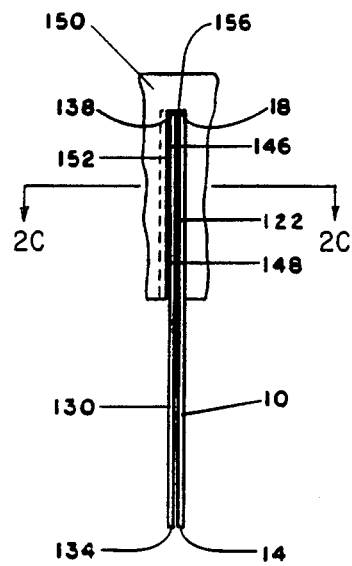

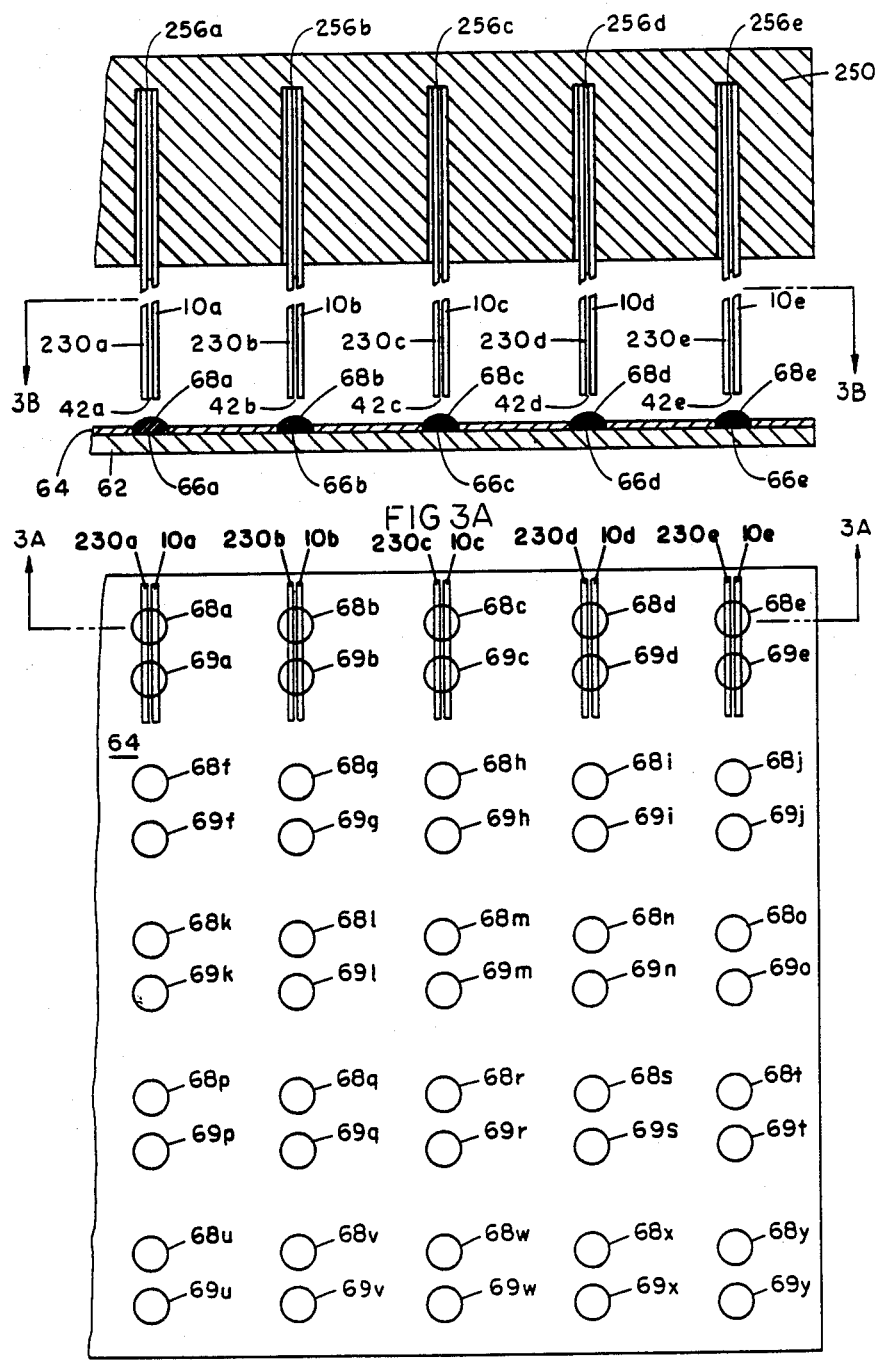

METHOD FOR TREATING THIN SAMPLES ON A SURFACE EMPLOYING CAPILLARY FLOW

The present invention relates to apparatus and methods for treating samples such as histology, cytology, or hematology specimens immobilized on a suitable flat surface such as a microscope slide with liquids such as: (1) chemical staining solutions or (2) dissolved reagents such as (a) antibodies or (b) labeled DNA or RNA probes, such reagents being used, respectively, for detection of antigens or nucleic acid sequences present in the immobilized sample.

In the present art of histology, cytology, and hematology, most clinical or research laboratories employ manual staining procedures which require many hours of technician time to perform. These procedures are usually cost effective because large batches of slides can be stained simultaneously in a single sequence of staining events by an individual technician. Both manual and automated staining systems in current use sequentially immerse a holder containing parallel slides with tissue or cellular smears immobilized on one planar surface of each slide in an identical series of liquid reagents such as aqueous reagents or organic solutions of dyes or stains in a routine or programmed fashion. Exemplary manual staining systems for histology, cytology, and hematology specimens are well known to the art of histo- and cytopathology, and protocols for their performance can be found in any laboratory performing staining on immobilized specimens. Exemplary automated systems include those sold by Technicon Instruments, Shandon Southern and Fisher Scientific (see pages 426-427 of the Fisher 86 Catalog for a description of the Fisher Histomatic ® Slide Stainer Model 172).

Capillary action has been used in the following prior art patent in an attempt to develop bulk automated slide staining proceudres. U.S. Pat. No. 4,199,613 to Johnson (1980) describes a system wherein a stack of parallel slides are engaged near both ends by a series of generally parallel shims. The shims are between corresponding ends of adjacent slides being stacked in parallel so as to space the facing planar surfaces of adjacent slides by the thickness of the shims. Such thickness (e.g., 0.008 inch or 0.2 mm) provides a spacing between such opposite planar faces of adjacent slides suitable for capillary flow. In use, a set of slides (e.g., 50) is held in a vertical stack; and a continuous stream of liquid (e.g., staining solution) flows over adjacent edge portions of the slides (starting with the top slide in the vertical stack) and fills successively the thin gaps between adjacent slides. The filling is by capillary flow in a horizontal direction. Excess liquid over that required to fill the thins gaps flows off of the bottom slide. This system is intended to stain a multiplicity of slides with an identical series of reagents which is the same strategy used in manual and automated staining procedures noted above.

In the field of trapping liquid specimens in a microscopic viewing space, which field is not admitting to be analogous with the treatment of immobilized samples by liquid stains and reagents, capillary flow is often used. Generally, as in U.S. Pat. Nos. 4,501,496 to Griffin (1985) and 3,961,346 to White (1975), liquid sample is introduced onto a bottom plate and migrates by capillary flow into a thin gap defined by a viewing surface of the bottom plate and an overlaying clear plate. In U.S. Pat. No. 4,308,028 to Elkins (1981), however, a device called a strip is immersed vertically-extending into a sample such as a centrifuged urine sample in a tube. As described at col. 4, line 53-col. 5, line 14 (see FIGS. 6 and 7 of Elkins), a particulate-rich aliquot from the bottom fraction of the sample flows by capillary action into a chamber (identified as 14 in the Figures of Elkins). Elsewhere in Elkins, the construction of the strip by lamination of multiple layers (one middle layer being short and of defined thickness, at least one other layer being long and transparent) is described. Col. 7, lines 3-45. At the completeion of the method, the sample in chamber 14 of approximately the defined thickness is viewed unstained and untreated as indicated by FIG. 22 of Elkins through a portion of a long transparent layer which extends beyond the end of the short middle layer.

BRIEF DESCRIPTION OF THE DRAWING

FIG. 2A is a side elevational view of a disassembled slide pair according to a second embodiment of the present invention.

FIG. 2B is a view similar to FIG. 2A of the same slide pair assembled within a holder portion into a slide assembly.

FIG. 2C is a top view of the slide assembly in a holder taken in section along line 2C—2C in FIG. 2B.

FIG. 3A is a side elevational view, taken in section along line 3A—3A in FIG. 3B, of an array of slide assemblies above a droplet holder device, each according to the second embodiment of the present invention.

FIG. 3B is a plan view of the droplet holder device shown in section in FIG. 3A, taken along line 3B—3B in FIG. 3A.

SUMMARY OF THE INVENTION

Figure 1A:
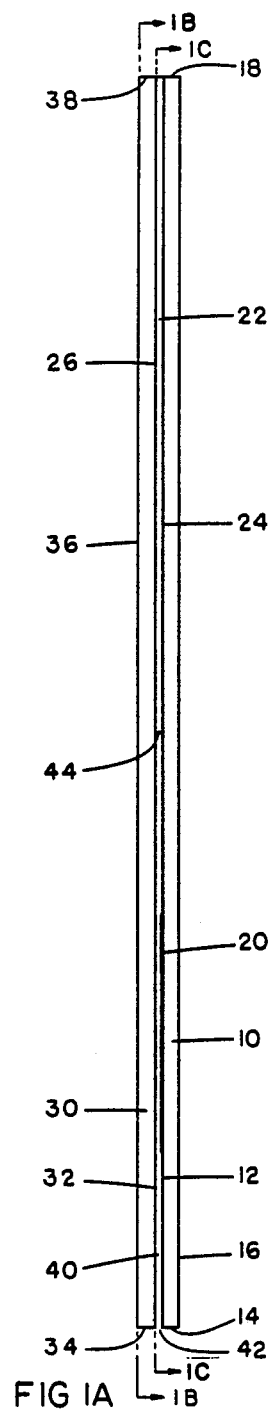
FIG. 1A is a side elevational view of a slide assembly according to a first embodiment of the present invention.

The various methods and apparatus provided in the present invention enable multistep treatment of a thin sample or material immobilized on a flat surface with the advantage of either conservation of expensive liquids, flexibility in varying the treating liquids for concurrently-treated samples or materials, minimization of cross-contamination between samples, safety in preventing toxic reagents from contacting laboratory personnel or some combination of these factors. In the present method, such advantage or advantages are achieved: by the use of a thin capillary gap in front of the surface containing the immobilized sample, especially when the gap extends vertically, by contact of an edge of the gap with a discrete aliquot of the treating liquid, especially at the base of the vertically-extending gap, or by the subsequent removal of the liquid by contacting an edge of the gap with an absorbent material, especially the bottom edge of a vertically-extending gap, or, especially, by combinations of these features. Such features offer particular advantages over the method of U.S. Pat. No. 4,199,613, which cannot concomitantly treat individual slides with unique reagents and which employs, by contrast, a horizontally-extending gap, introduction of liquid as a continuous stream and removal of liquid by spinning the entire slide assembly.

Although the present invention may be used for bulk staining wherein a multiplicity of slides are exposed serially to a single sequence of liquid reagents, it has particular advantages over the prior art when used as a discrete analyzer in which individual slides have their own unique series of reagents applied concomitantly to them.

Accordingly, the present invention provides, in one form, a method for applying liquid to a thin sample on a first surface which comprises the steps:

(a) maintaining a second surface substantially parallel to and spaced by a first distance from the first surface, thereby providing a gap between the first and second surfaces, and (b) contacting an edge of the gap with a discrete aliquot of liquid, the first distance being sufficiently small to cause liquid to migrate by capillary action within the gap into contact with the thin sample.

The present invention further provides, in a second form, a method for treating a thin sample on a first face with a series of treating liquids which comprises the steps:

(a) drawing a first treating liquid by capillary flow in a gap between a sample-bearing first surface and a second surface of a facing element to at least the position of the sample immobilized on the sample-bearing first surface, (b) retaining the first treating liquid by capillary action in the gap in contact with the sample, (c) removing the first treating liquid from the gap by capillary flow, and (d) drawing a second treating liquid by capillary flow in the gap to at least the position of the sample.

The present invention further provides, in a third form, an apparatus for treating a thin sample on a first surface which comprises:

(a) engagement means for holding a first member having a sample-bearing first surface a fixed distance from a second surface of a facing element, with the first surface and second surface being maintained substantially in parallel and with first and second edges of the two surfaces extending in parallel and being separated by substantially the first distance, and (b) contacting means for contacting the space between the first and second edges with a discrete aliquot of a liquid, the first distance being sufficiently small for liquid to migrate from the space by capillary action between the first and second surface into contact with the sample.

The present invention further provides, in a fourth form, an apparatus for treating a thin material on a planar surface which comprises:

(a) engagement means for holding a material-bearing planar surface in a vertically-extending position a first distance from a surface of a facing element, the engagement means maintaining alignment between the facing planar surfaces such that the lower edges of the material-bearing planar face and the facing planar surface are horizontally extending and substantially parallel, and (b) contacting means for contacting the space between the lower edges of the material-bearing planar surface and of the facing planar surface with liquid, the first distance between the material-bearing planar surface and the facing planar surface being sufficiently small for the liquid to migrate upwardly by capillary action between the facing planar surfaces to at least the height of the thin material.

In each of the first four forms of the present invention, the second surface (or surface of the facing element) may also bear a thin sample or material which is contacted by the same treating liquid as is the thin sample or material on the first surface (or material-bearing planar surface). Furthermore, or alternatively, an array of multiple pairs of surfaces may be arranged so that liquid is drawn by capillary action into the gap between each pair of surfaces simultaneously, concurrently or concomitantly.

The present invention further provides, in a fifth form, an array of slide assemblies comprising:

(a) a plurality of vertically-extending slides, each having a vertically extending face, (b) a plurality of vertically-extending cover members, each having a vertically-extending face, each face of a vertically-extending slide being spaced by a first distance less than 0.5 mm from a face of a vertically-extending cover member, and (c) engagement means for holding the vertically-extending slides and vertically-extending cover members adjacent to their upper ends in a fixed array with the sample face of each slide being a first distance from a substantially parallel face of a vertically-extending cover member and with the lower edge of each slide extending horizontally and being spaced from a substantially parallel horizontally-extending lower edge of a cover member by the first distance, the space between the horizontally-extending lower edges being open.

The present invention further provides, in a sixth form, a device for holding a horizontal array of discrete aliquots of treating liquid comprising:

(a) a horizontally-extending rigid base, (b) a horizontally-extending elastomeric member having a substantially planar horizontally-extending upper surface, and (c) a plurality of recesses formed in the elastomeric member, each recess opening to the horizontally-extending upper surface, the elastomeric member having at its upper surface a material sufficiently incompatible with the treating liquid for a discrete aliquot of treating liquid in a recess to form a convex shape extending above the plane of the adjacent upper surface of the elastomeric member.

Although above-described systems, such as that of Johnson, are capable of applying a specific sequence of identical reagents to a set of flat surfaces such as microscope slides, such prior art systems do not have the flexibility to concommitantly process individual slides with unique reagents. In addition, the volumes required to immerse the slides in a vessel of aqueous or organic stain are too great to economically perform specific steps of more sophisticated analyses of tissue or cellular bound antigens or genetic sequences, by antibody-directed detection technology or nucleic-acid-hybridization methodologies, respectively. Any multistep process involving such specific steps can only be automated by the proir art systems by performing the other steps, disassembling the slide array to perform the specific steps manually, and then reassembling the slide array to perform the subsequent steps automatically. Such disassembly/reassembly defeats the advantages of automation for such sophisticated analyses. Therefore, there is a need, met by the present invention, for either manual or automated methods that perform simultaneous, multiple, and discrete analyses on separate tissues or cellular smears immobilized on individual slides using only microliter quantities of expensive antibodies or nucleic acid probes.

DETAILED DESCRIPTION OF THE INVENTION

Such methods would have a wide spectrum of applications in both clinical or research laboratories that presently perform the analysis of discrete antigenic or genetic information by individual manual procedures.

Figure 1B:
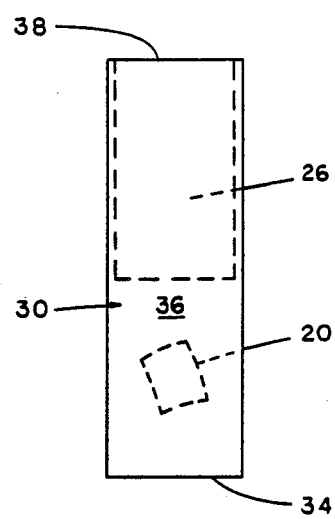
FIG. 1B is a front elevational view taken along lines 1B—1B in FIG. 1A.
Figure 1C:
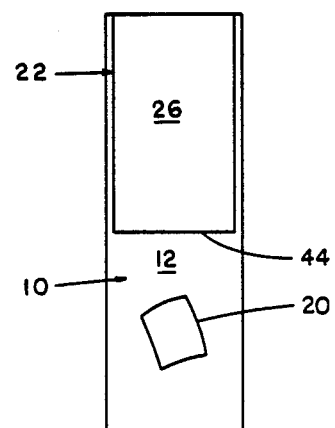
FIG. 1C is a front elevational view, in section taken along line 1C—1C in FIG. 1A.

A first embodiment of slide pair assembly is shown in FIGS. 1A, 1B and 1C. Referring to FIG. 1A, the sample-bearing microscopic slide 10 has a sample-bearing front surface 12, a first lower edge 14, a back surface 16 and a top edge 18. A thin sample 20, such as a 5-10 micrometer thick histology specimen, is provided on a lower portion of the front surface 12. Assuming that the slide is 75 mm high, 25 mm side and 1 mm thick (standard dimensions for a microscope slide), the sample can be a 20 mm×20 mm square located at least 1.0 mm (e.g., 10 mm) mm above the first lower edge 14.

Attached to the upper portion of the front surface 12 of the first slide 10 is a shim 22, shown in this first embodiment as two-sided adhesive tape of thickness 0.2 mm (200 micrometer). One sticky side 24 of the shim 22 adheres to the top portion of front surface 12 of first slide 10. The opposite sticky side 26 of shim 22 adheres to a facing surface 32 of facing element or slide 30. In this embodiment, facing slide 30 is also a 75 mm×25 mm×1 mm microscope slide. The shim 22 holds facing slide 30 in alignment with first slide 10 such that: facing planar face 32 of facing slide is parallel to front surface 12 and spaced therefrom by the thickness of shim 22 (200 micrometers), second lower edge 34 of facing slide 30 is coplanar with first lower edge 14 of first slide 10, back surface 36 of facing slide 30 is parallel to surfaces 32, 12 and 16 and top edge 38 of facing slide 30 is coplanar with top edge 18 of first slide 10.

The spacing of 200 micrometers is substantially constant from between the inner edges of top edges 18 and 38, along the vertical lengths of front surface 12 and facing surface 32, and to the inner edges of first and second lower edges 14 and 34. Assuming that the tape is 25 mm high (its width can be the full 25 mm width of slides 10 and 30, or can be less, e.g., 22 mm as shown), then a gap 40 is formed between the front surface 12 and the facing surface 32. This gap 40, which is 50 mm high, 25 mm wide and 0.2 mm (200 micrometers) thick, is the capillary gap terminating in lower end 42. The sample 20, being only 5-10 micrometers thick, has no significant impact upon the thickness of the gap 40, even at the height of the sample 20. Similarly, other imperfections, entrapped particles, angling of the two slides toward or away from parallel, or other factors that affect the gaps 40 by less than 20% (i.e., cause the 200 micrometer thick gap to remain between 160 and 240 micrometers in thickness) have no adverse impact, and even slightly larger variations would have no significant adverse impact. Furthermore, while the basic or average thickness of the gap in this first embodiment is 0.2 mm (200 micrometers), gaps as small as 0.05 mm (50 micrometers) or as large as 0.5 mm (500 micrometers) are permissable, with other dimensions (such as height) adjusted as described below in relation to FIG. 4. Under appropriate circumstances, thickness of the gap still less than 50 micrometers or more than 500 micrometers may also be appropriate.

FIG. 1B shows the same slide pair assembly from the front. The facing slide 30, with its back surface 36 on front, completely covers the first slide 10, from the top edge 38 to the bottom edge 34 of the facing 30. Sticky side 26 of shim 22 can be seen under the top portion of facing slide 30; and sample 20, which is immobilized on sample slide 10, can be seen centered under the lower portion of facing slide 30. The precise vertical alignment shown in FIG. 1B, wherein neither side of first slide 10 extends beyond the corresponding side of facing slide 30, is not critical. Misalignment in such direction of 2 mm, or even 5 mm, is of no significant adverse impact. Furthermore, as indicated above, the widths need not all be equal (e.g., 25 mm).

FIG. 1C shows the same front view as FIG. 1B, but now in section so as to look behind facing slide 30. The front face 26 of shim 22 occupies the top 25 mm of the visible surface. The bottom 50 mm×25 mm of front surface 12 of first slide 10 (below lower end 44 of shim 22) is now visible; it is this 50 mm×25 mm that is exposed to the capillary gap 40. The sample 20 occupies a 10×10 mm portion centrally located within this 50 mm×25 mm portion of sample-bearing surface 12. The height of the gap can be adjusted by using shorter or longer pieces of tape as shim: e.g., 25 mm wide and 20, 30, 40 or 50 mm long (high) tape.

FIGS. 2A, and 2B and 2C illustrate a second embodiment of slide pair assembly. First slide 10 with first lower edge 14, front surface 12 and sample 20 thereon is identical to corresponding elements in FIG. 1A. The facing slide 130 is also a 75 mm×25 mm×1 mm microscope slide, with facing surface 132 and second lower edge 134, but now the shim 122 is a 40 mm×25 mm (or 22 mm)×0.15 mm glass cover slip having a lower end 144. The first 40 mm×25 mm surface 124 of shim 122 faces (and, when assembled in FIG. 2B abuts against) the upper portion of front surface 12 of first slide 10. The second 40 mm×25 mm surface 126 of shim 122 is glued to the upper portion of facing surface 132 of facing slide 130.

Along the back surface 136 of facing slide 130 are provided upper and lower elastomeric protuberances 146 and 148, shaped as O-rings, compressible flat springs or rollers or solid discs, which may have beveled upper portions (not shown).

In FIG. 2B, the slide pair of FIG. 2A is assembled by placing slides 10 and 130 together in parallel and slipping their upper ends into a recess of dimensions 30 mm high, 26 mm wide and 2.4 mm thick formed in holder 150. The recess opens downwardly and has, on its top, a vertically-extending aligning face 156. Top edges 18 and 138 of first slide 10 and facing element 130 abut against aligning face 156. Protuberances 146 and 148 are engaged within a vertically extending, downwardly-opening slot 152 within the back wall of the recess formed in holder 150, so as to force the upper portion of facing element 130 and all of shim 122 against the upper portion of first slide 10. This combination of engagement means causes the first slide 10 and facing slide 130 to be aligned in parallel, with a gap the thickness of shim 122 (0.15 mm), the width of slides 10 and 130 (25 mm) and the height (35 mm) not covered by shim 122. Lower edges 14 and 134 are at the same height and are spaced from each other by substantially the same distance as the thickness of shim 122, i.e., 0.15 mm.

FIG. 2C is a top view of FIG. 2B taken along line 2C—2C in FIG. 2B. In this sectional view, protuberance 148 is seen inside its slot 152 which is cut into the slide holder 150 as a downwardly open slot in the recess. Protuberance 148 presses against slot 152 and compresses shim 122 which is glued to the opposite side of facing element 130. This in turn exerts pressure on the upper portion of the first slide 10 which is held in place by holder 150. In this manner the upper portion of the facing slide 130 and the first slide 10 are kept in contact and suspended vertically below. Since slot 152 is downwardly open, the facing slide 130 and the first slide 10 may be easily inserted into and removed from the recess in the holder 150 by the guiding action of slot 152 on protuberances 146 and 148.

Figure 2D:
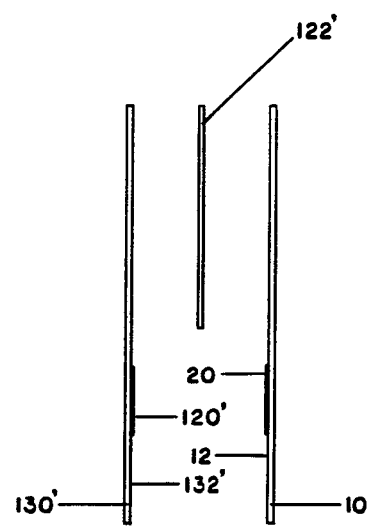
FIG. 2D is a view similar to FIG. 2A of a disassembled slide assembly according to a third embodiment of the invention.
Figure 2E:
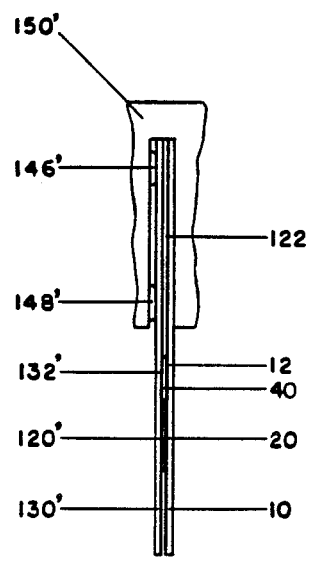
FIG. 2E is a view similar to FIG. 2B of the slide assembly of FIG. 2D in a holder.

FIG. 2D and 2E illustrate a third embodiment differing from that of FIG. 2A in that the protuberances 146' and 148' are now located on the interior of the recess within the holder 150' rather than on the back surface 136 of facing element 130.

Referring to FIG. 2D, the sample-bearing microscope slide 10 has its sample bearing front surface 12 facing a second sample bearing microscope slide 130' and its sample-bearing surface 132'. Thin sample 20 on sample bearing microscope slide 10 is present opposite sample 120' on the opposite sample-bearing slide 130'.

Referring to FIG. 2E, sample-bearing slides 10 and 130' are held in place in the recess in holder 150' by the pressure of the elastomeric protuberances 146' and 148' pressing against their upper portions. Shim 122' is sandwiched in between their upper portions. Sample 120' immobilized on sample bearing surface 132' of the second sample bearing slide 130' is held in the gap 40 produced by the close apposition of the sample-bearing surfaces held in place across and on the opposite side of the gap 40 from sample 20 by the pressure of protuberances 146' and 148' and the holder on the upper portions of the two sample bearing slides 10 and 130' against shim 122'.

FIGS. 3A and 3B show how an array of twenty-five slide pairs can be aligned and used in accordance with the present invention. Referring to FIG. 3A, one row of five slide pairs is shown. Each pair of first slide (10a, 10b, 10c, 10d, 10e) is spaced from a second or facing slide (230a, 230b, 230c, 230d and 230e) by a shim. Vertical alignment is maintained by the upper edges (256a, 256b, 256c, 256d and 256e) of five recesses formed in the bottom face of holder 250.

Thus vertically-extending gaps of the thickness the shim are formed in each slide pair, as described above in relation to FIGS. 2A and 2B, terminating in lower spaces 42a, 42b, 42c, 42d and 42e between, respectively, aligned first and second lower edges of the first and facing slides 10a/230a, 10b/230b 10c/230c, 10d/230d and 10e/230e. All sets of lower edges are in a common horizontal plane a fixed distance below the lower face of holder 250.

Figure 7:
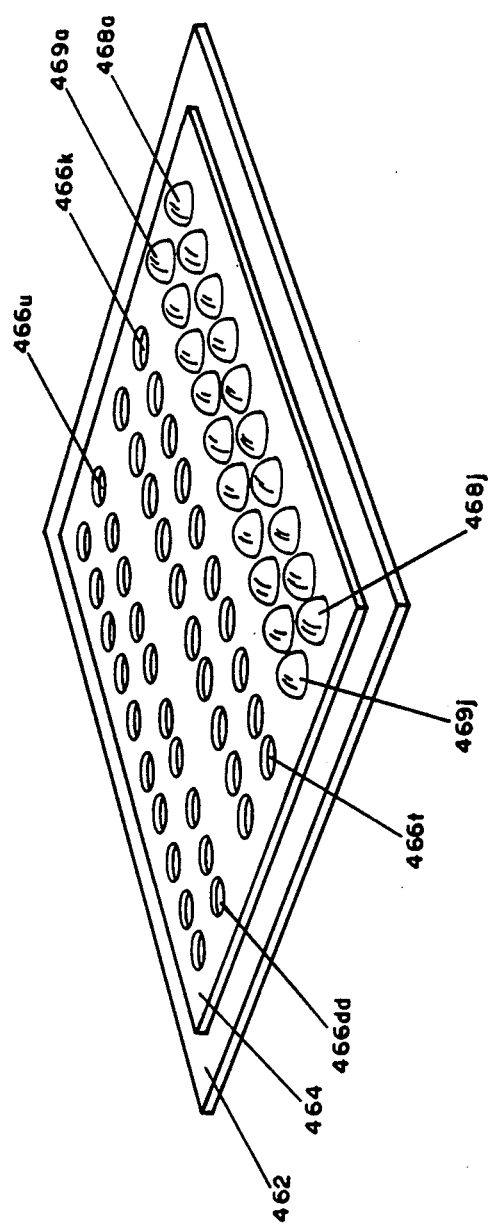
FIG. 7 is a persepective view of a partially-filled droplet holder according to the embodiment of FIGS. 5 and 6.

A droplet holder is located below this horizontal plane, consisting of a rigid base 62 and a horizontally-extending elastomeric member 64. As shown in FIG. 3A, five holes 66a thru 66e are formed in and through elastomeric member 64, and these holes are filled with discrete aliquots or droplets 68a through 68e, respectively, each of defined volume, e.g. 150 microliters. As described more fully below, each droplet 68a–68e projects above the top face of elastomeric member 64. The alignment is such that, when the slide holder 250 is lowered, lower spaces 42a–42e are contacted by the upper portions of droplets 66a through 66e, respectively. The droplets are normally introduced from above (e.g., by a micropipetting device), but can also be introduced from below by means of a narrow passage formed in rigid base 62. A perspective view of an analogous droplet holder is shown in FIG. 7.

Referring to FIG. 3B, the top of elastomeric member 64 can be seen with five double rows of droplets 68a–68y and 69a–69y. Looking at the profiles of slides 10a–10e, with facing slides 230a–230e, it can be seen that they will contact droplets 68a–68e and 69a–69e, with, for example, lower space 42a contacting droplets 68a and 69a near the two ends of lower space 42a.

Just as the one row of slide pairs 10a/230a through 10e/230e contacts droplets 68a–68e and 69a–69e, four additional rows of five slide pairs each can be aligned within holder 250 so as to contact, respectively: (2) droplets 68f–68j and 69f–69j, (3) droplets 68k–68o and 69k–69o, (4) 68p–68t and 69p–69t, and (5) 68u–68y and 69u–69y. Because the lower edges of all first slides, facing slides and thus lower spaces can be held in precise alignment within a common horizontal plane, and elastomeric member 64 holds the entire array of droplets in precise alignment within a common horizontal plane, one can reproducibly contact each lower space between first and second lower edges of a first and facing slide, respectively, with two droplets. Furthermore, as discussed below, the discreteness of droplets 68a–68y and 69a–69y enables flexibility in treating samples on each first slide either similarly or differently than each other first slide as to the treating liquid applied.

Figures 3C, 3D:
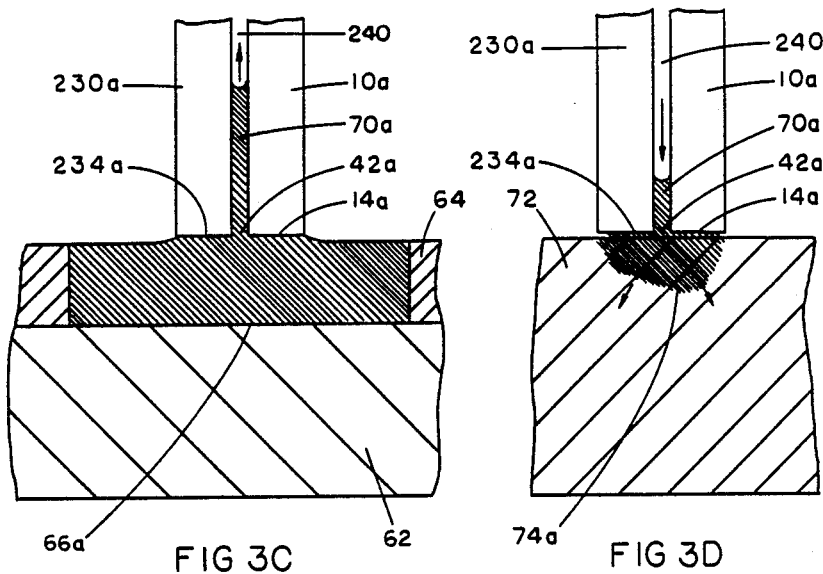
FIG. 3C is a magnified view of one slide assembly contacting one droplet, from an angle similar to that of FIG. 3A, showing liquid being drawn vertically into the thin gap by capillary flow according to the methods of the present invention.
FIG. 3D is a view, similar to that of FIG. 3C, of liquid being drawn vertically out of the thin gap by capillary flow into an absorbent material.

Referring now to FIG. 3C, the effect of space 42a (between first lower edge 14a and second lower edge 234a of slides 10a and 230a) being contacted by a droplet in hole 66a can be seen. A capillary column of liquid 70a rises in the capillary gap 240 (similar to gap 40 in FIG. 1A) by capillary action. This effect is enhanced by the relative incompatability of the liquid with the surface of elastomeric member 64, e.g., because the aqueous droplet is repelled by the hydrophobic surface of elastomeric member 64. Such incompatability (evidenced by beading of the treatment liquid if it were placed on a flat surface of elastomeric material used for member 64) also causes the droplets to stand above the top surface of member 64.

After the capillary column 70a has risen as far as capillary action will take it (typically about 30 to 40 mm in the indicated gap of 0.15 mm), the slide assembly can be lifted by holder 250 away from elastomeric member 64. Each slide pair (e.g., 10a/230a) will hold, by capillary action, the treating liquid received from the droplets (e.g., 68a and 69a) with which its lower space (e.g., 42a) has been contacted. After the liquid has remained in the gap for a desired time period, the slide assembly is now lowered onto an absorbent material 72 as shown in FIG. 3D. Since the liquid is more compatible with the absorbent material 72 than with the surfaces of slides 10a and 230a, now the capillarly column 70a will descend, with the treating liquid spreading downward and outwardly as a liquid front 74a within absorbent material 72. Within a matter of seconds, the slide pair will be evacuated essentially completely of liquid by such capillary action, except perhaps for minute amounts that may adhere to the sample or to other hygroscopic surfaces along the slide gap 240 or lower edges 14a and 234a. Once the liquid is evacuted from the slide gap 240, the slide pair may now be moved to another droplet holder, or to a sheet or bath of treating liquid for the next step.

Figure 4:
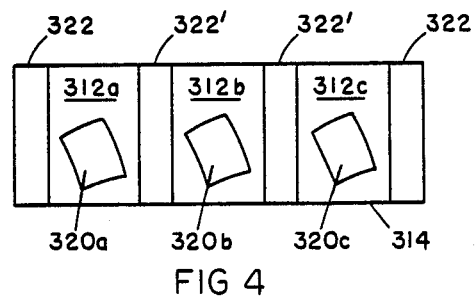
FIG. 4 is a front elevational view in section, similar to that of FIG. 1C, of a slide assembly according to a fourth embodiment of the present invention.

FIG. 4 illustrates, in a view similar to that of FIG. 1C, an embodiment of the invention wherein three vertically-extending sample-bearing surfaces are formed on one 75 mm×25 mm slide. The slide extends horizontally with its 75 mm lower edge 314. Two outer shims 322 of 25 mm height, 2 mm width and 0.25 mm thickness extend vertically on the front (75 mm×25 mm) face. Two inner shims 322' have similar 25 mm×2 mm×0.25 mm dimensions, and are equally spaced from and parallel to end shims 322. Such shims 322 and 322' can be formed by applying a thermosetting material (e.g., epoxy or silicone) to the face of a glass slide. The uncovered and isolated faces are therefore 312a, 312b and 312c, each extending upwardly 25 mm from lower edge 314, and each approximately 22.33 mm in width. A facing slide can be placed over this first slide, so that gaps of 0.25 mm thickness, 25 mm height and 22.33 mm width will form over faces 312a, 312b and 312c. By contacting the lower space of each such face which is adjacent to lower edge 314 by a treating liquid and then by an absorbent material, liquid reagent can be drawn into and out of each gap as described above. Such a slide pair can be applied to droplets or to a bath or sheet of treating liquid manually.

Alternatively, a series of such horizontally-extending slide pairs, each with three vertically-extending capillary gaps, can be held within a holder using, for example, the slide rack shown in FIG. 1 of U.S. Pat. No. 4,199,613 of Johnson, with such modification as is required to leave lower edges 314 of each sample-bearing slide available for contact by droplets or sheets of treating liquid. The "shims" of Johnson in this embodiment would not be positioned between a sample slide and its companion facing slide to help form the capillary gap between them, but would rather be located at both lateral ends and on the outer surface of the facing sample bearing slides, forcing them together by compressing the facing slide and the sample bearing slide against shims 322 described above. In this embodiment, shims 322 and 322' in FIG. 4 would be the only parts defining the first distance of the capillary gap between the facing and sample bearing slide.

The thickness of the side walls of the recess in the holder would then define a second distance separating parallel pairs of facing and sample bearing slides. This second distance is not designed for capillary action and separates sets of slide pairs so that liquid reagents can be drawn up into them through the capillary gap from discrete droplets as in FIGS. 3A and 3B. This second distance can be any thickness greater than 2 mm, which is significantly thicker than the 200 microns of Johnson's shims or the shims described in this patent. The preferable length of this second distance and, therefore, the preferable thickness of the side walls forming the borders of any downwardly open slide recess in the slide holder, ranges from 5 to 7 mm. Using this range, the greatest number of slides can be engaged into a slide holder for the purpose of drawing up, incubating and removing liquid reagents from the capillary gaps between adjacent slide pairs.

This second distance range allows adjacent capillary gaps such as 42a and 42b in FIG. 3A to be maintained from 7 to 9 mm apart. At this distance, individual droplets in the droplet holder such as 68a and 68b and 69a and 69b pictured in FIG. 3B can be maintained apart without contaminating each other by inadvertantly overcoming the incompatibility of the surface of elastomeric member 64 and the individual droplets in the droplete holder. Such advantage would not be possible with the slide rack of Johnson where 200 microns is too close to stably separate adjacent reagent droplets on the droplet holder. Therefore, the slide rack of Johnson would have to be completely and substantively modified from its original description to achieve the advantages of the present invention.

To cause the liquid to rise 15-20 mm above lower edge 314, the gap (thickness of shims 322 and 322') may be thicker than the 0.15-0.20 mm thickness most preferred in the earlier embodiments, where liquid was intended to rise 25-45 mm above lower edge 14. Through routine experimentation, the gap can be adjusted (by varying shim thickness) to achieve the desired vertical rise of liquid for any sample-bearing slide surface.

Figure 5:
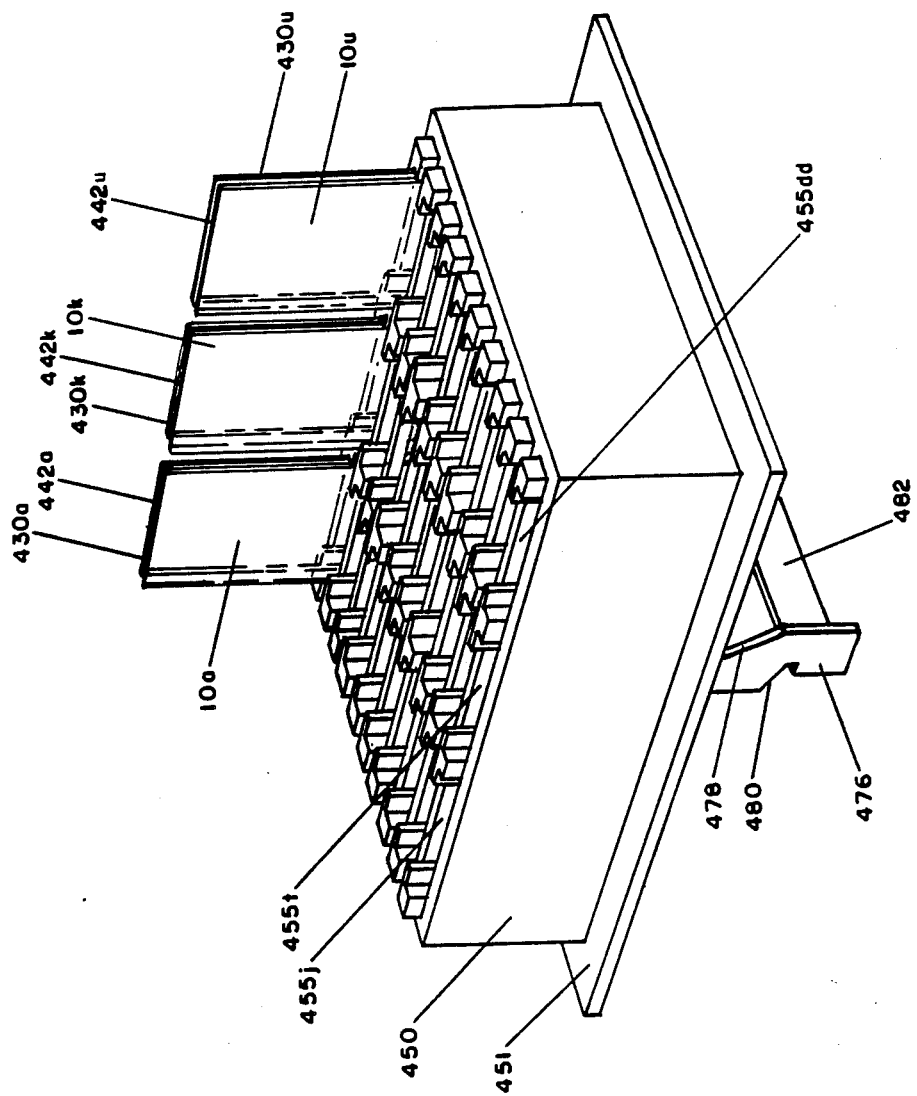
FIG. 5 is a perspective view of an inverted slide holder, partially filled with slide pairs, according to a fifth embodiment of the present invention, differing from the embodiment shown of FIG. 2A, 2B, 3A, 3B, 3C and 3D only in that the array is three rows of ten slide pairs rather than five rows of five slide pairs.

FIG. 5 shows a holder partially filled with slide pairs according to a fifth embodiment of the present invention. It differs from the second embodiment shown particularly in FIGS. 3A and 3B in providing three rows of ten slide pairs rather than five rows of five slide pairs.

The main body 450 of the slide holder shown in FIG. 5 is shaped as a rectangular solid with, as described below, a series of slots formed in its lower face for receiving slide pair assemblies.

Alternatively, the slide pairs may be held in a holder where the series of slots formed at its lower face are collapsible and can be tightened upon the top portions of the slide pair assemblies using, for example, a substantial modification of the slide rack of FIG. 1 of U.S. Pat. No. 4,199,613 of Johnson in which the "shims" are significantly thicker and used to separate slide pair assemblies and not to produce capillary action.

Because the slide holder is inverted in FIG. 5, compared to its configuration in use, for the insertion of slide pairs, this bottom face appears on top. In the following description, relative positions in use (e.g., slots in the bottom face) will be described.

A plate 451 is above main body 450 (as a flange) in both horizontal directions so as to cover a larger rectangular cross-sectional area than the rectangular cross-sectional area of main body 450. An arm 476 extends vertically upward from one side of plate 451, with two angled portions 478 and 480. A similar arm 476, with angled portions 478 and 480, extends vertically upward from the opposite side of plate 451, but is hidden from view. A horizontal bar 482 connects the two arms 476.

Formed in the bottom face of main body 450 are ten long slots, each extending vertically and in a horizontal direction 90° relative to horizontal bar 482. These ten long slots are each divided by partitions into three slots, for a total of thirty slots. The nearest three slots are designated 455j, 455t and 455dd in FIG. 5, each such slot being at the near end of a row of ten slots. Sample-bearing slides 10a, 10k and 10u are shown extending out of the slots at the far end of each of the three rows. As illustrated by facing slide 430u, a facing slide is inserted with each sample-bearing slide in a common slot. The bottom edges of each sample-bearing slide and the adjacent facing slide defines a lower end of a gap, shown as lower end 442a, 442k and 442u for slides 10a, 10k and 10u, respectively. Each individual slide pair appears in cross-section substantially as shown in FIG. 2B. If thirty sample-bearing slides are to be treated, then the remaining slots shown in FIG. 5 (up to slots 455j, 455t and 455dd) are filled and the entire slide holder assembly unverted. To keep track of the various slides, either visually- or machine-readable indicia may be present or applied (e.g., on a frosted portion of each slide remote from the sample) so as to be read before and after treatment, or (if the indicia are properly placed, e.g., just above the sample location) also while the slides are in the holder. Additionally, the holder may be indexed numerically to ease the localization of individual slides without taking them out of the holder and to ease reagent handling by having corresponding numbers denoting the specific holes in the droplet holder pictured in FIGS. 3B and 7 with which the slide pair assembly interacts.

The holder is then lowered into a bracket the width of horizontal bar 482 along angled portions 478 of arms 476 until the slide assembly is held and aligned (vertically and horizontally) by the engagement of the bracket with horizontal bar 482 and arms 476. The machine can now conduct the assembly through a series of stations as described below. Alternatively, the holder's horizontal bar 482 may be engaged manually and thereby advanced.

Figure 6:
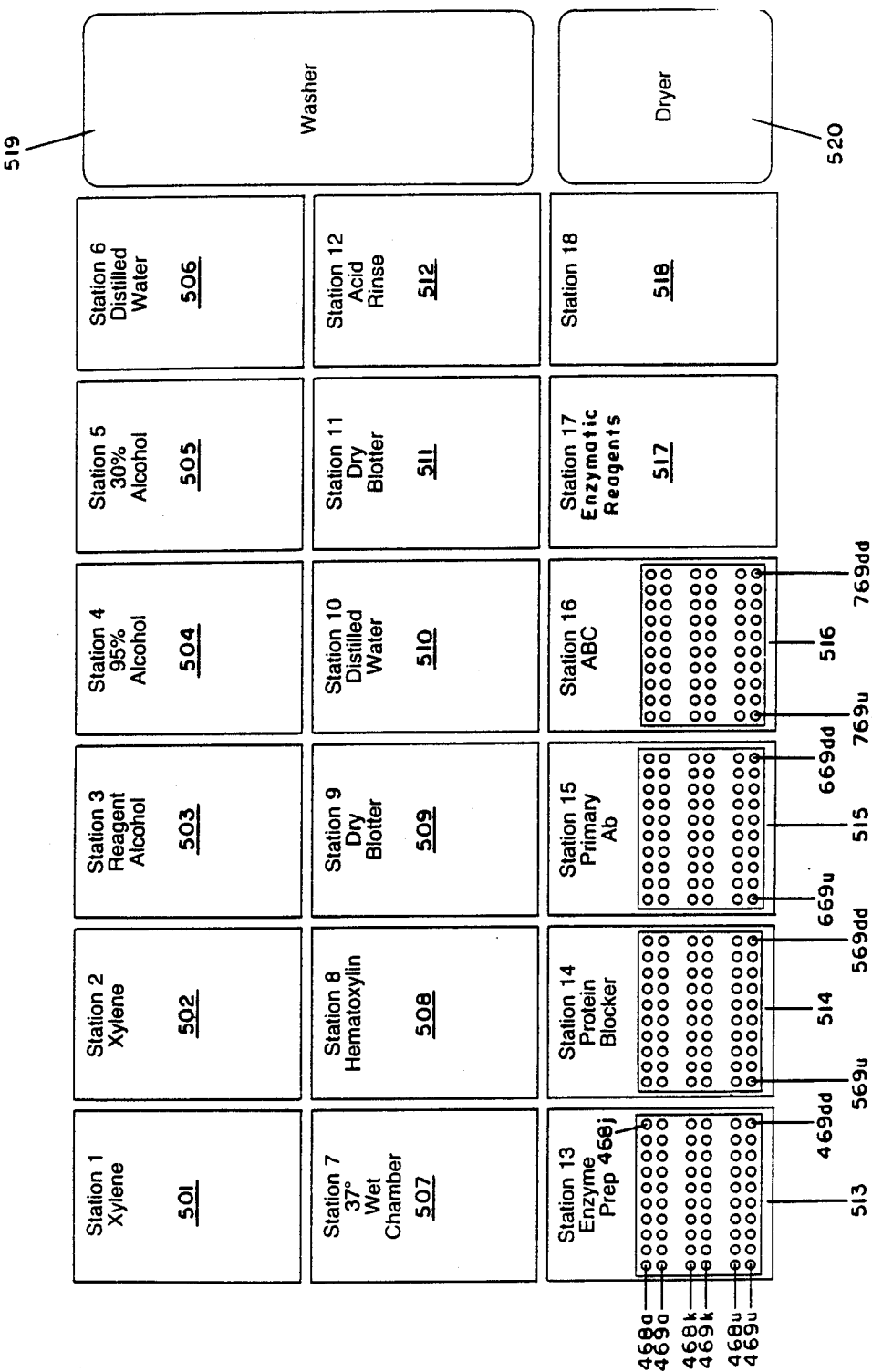
FIG. 6 is a plan view of an array of stations for either a manual or an automated multistep process employing the slide pairs array of FIG. 5.

FIG. 6 shows a plan view of the interior of an automated system for practice of the present invention. It resembles the interior of a HISTOMATIC® Slide Stainer (Model 172) as illustrated on page 426 of the Fisher 86 Catalog (Fisher Scientific 1985), modified for practise of the present invention.

FIG. 6 illustrates an array of stations into which the slide array of FIG. 5, once completely assembled, can be dipped by sequential operation as described below. Stations 1-6 (numerals 501 through 506) contain, in this arrangement, staining vessels of the general type previously used with the HISTOMATIC® slide stainer, Model 172 (115 V, 60 Hz version). See Fisher 86 Catalog, pp. 426-27 (Fisher Scientific 1985). Each vessel holds a pool of liquid (xylene, ethanol, ethanol/water mixtures or distilled water, as indicated) of top cross-sectional area being larger than the array of lower edges of slide pairs in FIG. 5. Such geometry permits the array to contact each pool without hitting a vessel edge. Similarly, stations 8 (numeral 508), 10 (numeral 510), 12 (numeral 512) and 17 (numeral 517) contain staining vessels of composition indicated below.

Station 7 (numeral 507) is a wet chamber maintained at 37° C.±5° C. (once enclosed as described below) by a standard electric heater, kept saturated by water vapor because a pool of water is placed in the chamber below the height reached by the lowermost horizontal surface of the slide array. The top of the wet chamber is of horizontal dimensions (rectangular or square) larger than the slide array in FIG. 5, but smaller than the flange 451 in FIG. 5. Accordingly, when the slide array 450 in FIG. 5 is lowered into the wet chamber in station 7 (numeral 507), the flange 451 (shown in FIG. 5) completes the enclosure of the wet chamber.

Stations 9 and 11 contain dry blotters such as paper, cotton or super-absorbent gauze pad with top surfaces sufficiently high and level to simultaneously contact lower spaces (see 42a in FIG. 2D) of the slide array when the array is lowered into the appropriate station. The slide array may, in such case, compress the blotter material down a short distance.

Station 13, 14, 15 and 16 (numerals 513, 514, 515 and 516) contain droplet holders similar to elements 62 and 64 in FIGS. 3A and 3B except that the holes and droplets are arranged in three double rows of ten. Thus, in station 13 (numeral 513), the top row of ten slides will contact, simultaneously, droplets 468a–468j and 469a–469j in the same manner described above for droplets 68a–68e and 69a–69e as shown in FIGS. 3A and 3B. The second double row, beginning with droplets 468k and 469k, will be contacted simultaneously by the lower spaces of a second row of ten slide pairs. The third double row, beginning with droplets 468u and 469u, and ending with droplets 468dd and 469dd, will be contacted simultaneous by the third row of ten slide pairs when the slide pair array is lowered into station 13 (numeral 513).

In similar fashion, stations 14 (numeral 514), 15 (numeral 515) and 16 (numeral 516) each contain a droplet holder, each holding in precise alignment three double rows of ten droplets (sixty droplets in each station). The lower row in FIG. 6 is identified as droplets 569u thru 569dd in station 14, 669u thru 669dd in station 15 and 769u thru 769dd in station 16. Station 18 (numeral 518) is empty in the array shown in FIG. 6. If additional treating steps are desired, it can contain a staining vessel, droplet holder or temperature bath, as appropriate, similar to another station described above.

Washer 519 is the standard unit for washing slide arrays provided with the HISTOMATIC® Slide Stainer, Model 172. It is equipped either for once-through flow of rinsing liquid or recirculation of treating liquid. The latter mode is generally used in the present invention. In actual work, this unit has been modified by a solenoid to provide for recirculating flow of rinsing liquid only when the slide array is in the washer and to provide no drainage instead of a continuous drainage as when the machine is operated in the flow-through mode. The dryer 520 is a station generally not used in the present invention (because of the use of blotting stations 509 and 511), but preferably present so that the instrument can also be used for conventional staining of slides arranged vertically-extending and separated one from another by a distance greater than 0.5 mm (e.g., 2.0 mm) when using a standard 40-place slide holder provided commercially with the above Model 172 Slide Stainer.

The flexibility of this invention is illustrated by the fact that all the staining vessels, droplet holders, and wet chambers are completely removable and interchangeable at the discretion of the user. Therefore, for example, the droplet holders of Station 13, 14, 15 and 16 (numerals 513, 514, 515, 516 of FIG. 6) can be easily replaced even with the instrument running, with a shallow common reagent tray to treat all slide pair assemblies with an identical reagent or an additional blotter to evacuate them or a wet chamber to incubate them. The flexibility of the present process is further illustrated by the following illustrative process for staining tissue sections with a respect to antigenic sites for antibody. The following staining procedure log refers to numerals in FIG. 6, as described above. Following the log are a discussion of several of the individual steps and a discussion of how the procedure would be modified to use three different types of tags: avidin biotinylated horseradish peroxidase complex, alkaline phosphatase linked to goat anti-mouse antibody and, as the initial probe, either a primary biotinylated heterologous primary antibody, an unlabeled monoclonal antibody, or a DNA or RNA strand linked to biotin in the manner of EPA No. 63,879 of Ward, Wildrop and Langner (Nov. 3, 1982, based on U.S. Ser. No. 255,223) or PCT No. 84/04970 of Ward, Leary and Brigati (Dec. 20, 1984, based on U.S. Ser. No. 503,298), both assigned to Yale University. See also *Proc. Nat. Acad. Sci.* vol. 80, pp. 4045–49 (1983); *Virology*, vol. 126, pp. 32–36 (1983).

The staining procedure begins with thin (e.g., 5 micrometer thick) slices of tissue which are cut from blocks of tissue that have been formalin fixed and then wax embedded in, e.g., a Histomatic ® Model 266 MP Tissue Processor (Fisher Scientific) (see U.S. Pat. No. 4,141,312 to Louder, issued Feb. 27, 1979). Each event is described below by number, station (and corresponding numeral in FIG. 6), time and solution or other treatment.

| Event | Station (FIG. 6 Numeral) | Time (min.) | Solution or Other Treatment |
|---|---|---|---|
| 1A | 1 (501) | 1.0 | Xylene |
| 1B | 9 (509) | 0.6* | Blot |
| 2A | 1 (501) | 1.0 | Xylene |
| 2B | 9 (509) | 0.6* | Blot |
| 3A | 1 (501) | 1.0 | Xylene |
| 3B | 9 (509) | 0.6* | Blot |
| 4A | 2 (502) | 0.6 | Xylene |
| 4B | 9 (509) | 0.6* | Blot |
| 5A | 3 (503) | 0.2 | Reagent Alcohol or Absolute Alcohol) |
| 5B | 9 (509) | 0.6* | Blot |
| 6A | 3 (503) | 0.2 | Reagent Alcohol (or Absolute Alcohol) |
| 6B | 9 (509) | 0.6* | Blot |
| 7A | 4 (504) | 0.6 | 95% Ethanol |
| 7B | 9 (509) | 0.6* | Blot |
| 8A | 12 (512) | 5.0 | Acid Alcohol |
| 8B | 9 (509) | 0.6* | Blot |
| 9A | 5 (505) | 0.2 | 30% Ethanol |
| 9B | 11 (511) | 0.6* | Blot |
| 10A | 6 (506) | 0.2 | Triton ® X-100 (0.1%) in distilled water |
| 10B | 11 (511) | 0.6* | Blot |
| 11A | 6 (506) | 0.2 | Triton ® X-100 (0.1%) in distilled water |
| 11B | 11 (511) | 0.2 | Blot |
| 12A | R (519) | 1.0 | Buffer (0.1 M Iris HCl, 0.1 M NaCl, pH 7.5, 0.01% Triton ® X-100) in the recirculating mode |
| 12B | 11 (511) | 0.6* | Blot |
| 13A** | 13 (513) | 0.6 | Enzyme Digestion |
| 13B** | 7 (507) | 2.0 | 37° C. Wet Chamber Solutions** |
| 13C** | 9 (509) | 0.6* | Blot |
| 14A** | R (519) | 2.0 | Buffer |
| 14B** | 11 (511) | 0.6* | Blot |
| 15A | 14 (514) | 0.6 | 0.25% Gelatin in 0.1 M Tris HCl, 0.1 M NaCl, pH 7.5 |
| 15B | 7 (507) | 2.0 | 37° C. Wet Chamber |
| 15C | 9 (509) | 0.6* | Blot |
| 16A | R (519) | 0.6 | Buffer |
| 16B | 11 (511) | 0.6* | Blot |
| 17A | 15 (515) | 0.6 | Primary Antibody (Biotin-labeled) |
| 17B | 7 (507) | 60 | 37° C. Wet Chamber |
| 17C | 9 (509) | 0.6* | Blot |
| 18A | R (519) | 2.0 | Buffer |
| 18B | 11 (511) | 0.6* | Blot |
| 19A | R (519) | 1.0 | Buffer |
| 19B | 11 (511) | 0.6* | Blot |
| 20A | 16 (516) | 0.6 | Avidin & Biotin-Alkaline Phosphatase Conjugate |
| 20B | 7 (507) | 10 | 37° C. Wet Chamber |
| 20C | 9 (509) | 0.6* | Blot |
| 21A | R (519) | 0.6 | Buffer |
| 21B | 11 (511) | 0.6* | Blot |
| 22A | R (519) | 2.0 | Buffer |
| 22B | 11 (511) | 0.6* | Blot |
| 23A | 17 (517) | 0.6 | BCIP & INT (Enzymatic Reagents) |
| 23B | 11 (511) | 0.6* | Blot |
| 24A | 17 (517) | 0.6 | BCIP & INT |
| 24B | 7 (507) | 10 | 37° C. Wet Chamber |
| 24C | 9 (509) | 0.6* | Blot |
| 25A | 17 (517) | 0.6 | BCIP & INT |
| 25B | 7 (507) | 10 | 37° C. Wet Chamber |
| 25C | 9 (509) | 0.6* | Blot |
| 25A | R (519) | 2.0 | Buffer |
| 26B | 11 (511) | 0.6* | Blot |
| 27A | 8 (508) | 6.0 | Hematoxylin Stain, Harris Modified |
| 27B | 9 (509) | 0.6* | Blot |
| 28A | 10 (510) | 0.6 | Triton ® X-100 (0.01%) In Distilled Water |
| 28B | 9 (509) | 0.6* | Blot |
| 29A | 12 (512) | 0.1 | Acid Alcohol (Differentiates Hematoxylin) |
| 29B | 11 (511) | 0.6* | Blot |
| 30A | R (519) | 2.0 | Buffer (blues Hematoxylin at pH 7.5) |
| 30B | 11 (511) | 0.6* | Blot |
| 31 | 6 (506) | 0.6 | Triton X-100 In Distilled Water |

*for each indicated blotting step, 0.6 minutes (36 second) was used due to a machine limitation. With reprogramming, most of the blotting steps will be reduced to 12 or 18 seconds.
**steps 13A–14B are required only in those procedures where a protein digestion step (e.g., with pronase, trypsin or pepsin, each with appropriate buffers and cofactors) is needed to expose the desired antigenic sites of the tissue. In the work with thin tissue samples, such steps were not generally needed and; therefore, these steps were omitted and the drop holder in station 13 was replaced with a flat pan holding 1% Bovine Serum Albumin in 0.1 M TrisHCl, pH 7.6 with 0.1 M NaCl.

In considering the above overall process, events 1–7 and 9–12 involve removing the wax and converting to an aqueous buffered medium. In those instances wherein frozen samples have been sliced into thin samples, step 1–7 and 9 are unnecessary (since no wax is present). The surfactant was included in steps 10, 11 and 12 to facilitate capillary flow of the more viscous fluids that follow. Step 8 is the step used to block endogenous alkaline phosphatase activity in the tissue. If another enzyme were used (i.e., in step 20), a different endogeneous enzyme blocking treatment would be used. For peroxidase as the enzyme in step 20, absolute methanol with 0.9% hydrogen peroxide might be used as the solution in station 18 for step 8. Acid alcohol in station 12 would still be used in step 29. For processing frozen sections, the slides are first fixed in cold acetone for 10 min. and then exposed to 0.01% Triton X-100 in distilled water for 0.6 min (station 10); blotted for 0.6 min. (station 11), treated with acid alcohol to block endogenous alkaline phosphatase enzyme activity (station 12) and then proceed through the remaining stain program depicted above, beginning at step 13.

Steps 13 and 14, as indicated above, have not generally been needed for most antigens of interest in tissue, but would be used for hard-to-access antigenic markers such as tissue bound immunoglobulins, keratin, viral antigens such as Cytomegalovirus, Adenovirus, and Hepatitis B virus surface and core antigens, and for procedures employing nucleic acid probes.

Step 15 involves applying a general protein to adhere to the non-specific protein binding sites found in most tissue specimens. Failure to block these sites will give undesired background levels due to non-specific adherence of the primary antibody or avidin or biotin-enzyme conjugate in steps 17 and 20. When a secondary antibody is used in step 20 (e.g., alkaline phosphatase conjugated goat-anti-mouse immunoglobulin antibody in cases where the primary antibody is unlabeled mouse monoclonal antibody) instead of an avidin-biotin alkaline phosphatase complex, the blocking action of non-specific proteins such as gelatin in step 15 may be insufficient to preclude non-specific binding of the secondary antibody. Accordingly, one can use normal (unsensitized) serum of the same species as the secondary antibody used in step 20 (i.e., unsensitized goat serum in the illustrative case). For DNA probe work, it may be desirable to apply non-specific DNA as well as protein in step 15.

Step 17 provides the primary antibody used to target the antigenic sites of interest. Generally, it is biotin labeled, but if a secondary antibody is used in step 20, then unlabeled antibody may be used in step 17. Alternatively, the primary antibody may be radioactively or fluorescently labeled. DNA or RNA probes (e.g., biotin-labeled) may also be used in step 17, provided that adequate pretreatment steps have occurred. In such case, after application (step 17A), the slide assembly should be placed in a chamber at temperatures high enough for denaturation (e.g., 100° C.) for a few minutes before placement in the 37° C. Wet Chamber (step 17B) for rehybridization. The washing steps represented by steps 18 and 19 in the above procedure may be significantly expanded in number and duration and variety of liquids for DNA probes. See, e.g., U.S. Pat. No. 4,533,628 to Maas (Aug. 6, 1985), and references cited therein.

Step 20, as shown, involves the crosslinking of the biotin chemically bound on the primary antibody to a second biotin moiety chemically bound to the detection agent such as an enzyme by the tetravalent egg white binding protein, avidin. Because of its improved stability, avidin (egg white Avidin from Vector Labs) was used rather than streptavdin. Provided that the proper pretreatments were used, other biotin-labeled detection systems could be used: e.g., horseradish peroxidase (HRP) or beta-galactosidase conjugate with biotin. HRP has the advantage of creating chromophoric enzymatic reaction products (e.g., polymerization products of diaminobenzidine tetrahydrochloride) which are more securely anchored in the tissue than are the chromophoric enzymatic reaction products produced with alkaline phosphatase [e.g., 3 bromo, 4 chloro, 5 indolyl phosphate (BCIP) and either Iodonitrotetrazolium (INT) or Nitro Blue Tetrazolium (NBT)]. The adherence of the alkaline phosphatase chromophores can be enhanced by omitting the Triton X-100 in stations 6 and 10, and by programming the instrument to go directly into an extra two rinse cycles in distilled water. (Station 10 followed by Blot Station 11). The slides are then transferred to Station 18 where a shallow tray of ammonia water is placed. The slides are then directly mounted in polyvinylpyrrolidone (PVP-40) at 400 mg per ml in 0.1 M Tris HCl, pH 7.5, with 0.1 M NaCl. HRP has the disadvantage, however, that the enzymatic reactants that would be required in steps 23–25 are unstable to light and are suspected carcinogens. Therefore, if HRP is used, then the program is preferably stopped at step 21 or 22 until fresh reagent is made up and placed in station 17. The program is then manually restarted. Such time is compensated for by a shorter incubation time in steps 24B and 25B. Furthermore, the enzymatic product is sufficiently insoluble for the slides, after step 31, to be taken back through stations 6, 5, 4, 3 and 2 (the reverse order of steps 1–7 and 9), with multiple contacts at some station and a blot after each contact. The resultant stained samples are now coated with xylene and ready for dry mounting, e.g., with Permount ® mounting medium.

One may alternatively use a fluorescent tag in step 20, e.g., avidin-fluorescein conjugate. In such case, steps 23–26 are not needed.

Steps 23–25 supply enzymatic reagents (BCIP plus INT) appropriate to produce insoluble chromagens with the enzyme tag (alkaline phosphatase) introduced in step 20. Step 27, 29 and 30 represent application and development of hematoxylin as a counterstain for nuclear visualization of the tissue in which the labeled antigenic sites are found.

In the above procedure, steps 17 and 20 employ particularly expensive regents and are therefore performed with droplet holder in stations 15 and 16, respectively. Such droplet holders would normally be used to conserve these reagents, even when all droplets are the same, so as to treat all samples identically in this step. In many cases, however, individualization is required, particularly with respect to the primary antibody in station 15, in these droplet holders. The partially-filled droplet holder shown in FIG. 7 illustrates how different liquids can be supplied as droplets in any desired pattern.

A rigid horizontally-extending base 462 supports a horizontally-extending elastomeric member 464. Sixty holes are provided through member 464 in three double rows of ten. The first double row is filled with twenty droplets of a first treating liquid, including 468a, 468j, 469a and 469j. The second and third double rows of holes, including holes 466k, 466t, 466u and 466dd are empty. They can be filled, if desired, with a second and third treating liquid, to be applied to different slide pairs while the first row of droplets is being applied to a first row of slide pairs.

When enzyme digestion is employed in step 13, a droplet holder would also be used in station 13 (513 in FIG. 6). Individualization in this step can be employed where it is desired to vary digestion type or degree (e.g., some droplets being buffer without pepsin, some with) at this point. Similary, in step 15, when more expensive blocking agents than gelatin are employed in station 14, or if the degree or type of blocking is a desired variable, then a droplet holder would be used in station 14.

While stations 8 and 17 are shown as trays, droplet holders may be used to provide individualization in steps 23-25 and 27 as well. Where adequate slides and specimens are available, it may be desirable to achieve a different color level of the enzyme-generated stain and of the counterstain for replications of equivalent samples so as to create a range of contrast levels from which to choose.

Even as to those steps where trays are used to apply moderately expensive treating liquid (e.g., the hematoxylin stain) the present invention uses less liquid then that the system of Johnson, et al. (which fills the majority of the 75 mm×25 mm capillary space) because only a portion (approximately 30-40 mm×25 mm) is filled in the present process. Drainage, furthermore, is greatly facilitated by blotting rather than spinning.

It is preferred to use absorbent materials of sufficient absorbent capacities and to use a sufficient number of absorbent material stations (stations 9 (509) and 11 (511) in FIG. 6) to absorb all of the various liquids to be drained from the slide gaps during the entire process. Alternatively, at a convenient point in the process (e.g., during Event 17B) each absorbent material may be replaced by a fresh absorbent material (in Stations 9 and 11); or, while one absorbent station is being used (e.g., Station 11 during steps 9B-14B) the absorbent material in the other station (Station 9) may be changed.

In preferred forms of the invention, the gap between the two surfaces is maintained in the vertical position and a discrete aliquot of liquid reagent contacts the space produced between the parallel lower edges of two facing surfaces, such as two glass microscope slides, and flows upwardly by capillary action to cover, in total or in part, the inner surface of the gap. After treatment, the liquid reagent can be removed from between the planar faces by contacting the space at any point with an absorbent material. In less preferred forms suction apparatus or similar liquid extraction systems may be used. Such method is particularly useful in streamlining complex treatment regimens that involve treating a large number of immobilized samples with a series of liquid reagents and require the sequential application and removal of one liquid reagent from the sample analytes prior to the subsequent exposure of the same analyte to next liquid reagent in the process. Such is also extremely useful when it is desirable to use minimal volumes of precious, hazardous, or expensive liquid reagents such as dissolved tagged or untagged antibodies, nucleic acid probes, radioactive materials, or biohazardous materials where it is desirable to minimize human contact.

There are other embodiments of the invention wherein the parallel surfaces, and thus the gap there between, are not vertical, but rather are inclined upwardly or are even horizontally extending. In each such case, the advantages of the present invention, attributable either to the contact of an appropriate edge of the gap by a discrete aliquot of treating liquid (permitting individualization), or to the removal of liquid from the gap by capillary action (e.g., by contact of the edge of the gap by an absorbent material, permitting multistep processing with rapid drainage of each liquid), or both, can be obtained in similar fashion to embodiments described above. Similarly, the substantially parallel surfaces need not be planar, but may, for example, be curved as in cylindrical or conical sections.

Both the vertical and horizontal embodiments of this invention have the same uses and advantages over prior art in manual stain technology as practiced routinely in clinical and research laboratories that presently perform the analysis of discrete antigenic or genetic information by individual manual procedures. These applications include, but are not limited to, the detection of antigens of diagnostic prognostic importance in human, plant, or animal tissues, cellular smears, or extracts immobilized on solid surfaces such as a glass microscope slides, nitrocellulose or cellulose acetate membrane filters, or flat organoplastic support. These applications further include screening of identical human, plant, or animal tissue and tissue extracts by nucleic acid hybridization technology for their specific genes and their RNA transcripts. These methods would also have application in special stain techniques wherein a laboratory would stain a single tissue for several different histochemical markers, such as but not limited to mucicarmine, silver, Gram, Giemsa, Papanicolaou, or other histologic, hematologic, or cytologic stains.

Alternatively, tissues from many different anatomic sites and species may be stained with a single series of reagents especially in situations where the reagents employed are expensive or available in only microliter quantities. The low volume requirements of such systems as the screening of a single tissue type with monoclonal antibodies direct from limited supernatants or ascitic fluids are ideal uses for a method and apparatus designed to treat a thin sample immobilized on a planar surface employing capillary flow in either a vertical or horizontal position.

I claim:

1. A method for applying liquid to a thin sample on a first surface which comprises the steps:
   (a) providing a thin sample on a first surface,
   (b) maintaining a second surface substantially parallel to and space by a first distance from the first surface, thereby providing a gap between the first and second surfaces,
   (c) contacting a single edge of the gap with a discrete aliquot of liquid, the first surface, second surface and gap extending in a substantially vertical direction and the single edge being a lower edge,
   the first distance being sufficiently small to cause liquid to migrate by capillary action within the gap and
   (d) drawing liquid upwardly by capillary action within the gap from the single lower edge of the gap into contact with the sample.

2. The method of claim 1 wherein the single lower edge of the gap is contacted with a plurality of discrete aliquots of liquid.

3. The method of claim 1 wherein the first distance is about 0.1 to about 0.3 mm and the thickness of the thin sample is less than about 0.020 mm.

4. The method of claim 1 wherein each discrete aliquot of liquid contacts only a single lower edge of a single gap.

5. The method of claim 1 wherein the first and second surfaces are planar.

6. The method of claim 5 wherein the single lower edge of the gap contacted by the aliquot is defined by substantially parallel linear edges of the first and second surface.

7. The method of claim 6 wherein the substantially parallel linear edges extend horizontally.

8. The method of claim 7 wherein the first and second surfaces extend vertically upward.

9. The method of claim 1 further comprising the step:
(d) removing liquid from the gap.

10. The method of claim 9 wherein liquid is removed by contacting the single lower edge of the gap with an absorbent material.

11. The method of claim 1 wherein the providing step (a) the first surface is the face of a sample-bearing microscope slide.

12. The method of claim 11 wherein the maintaining step (b) the second surface is the face of a facing microscope slide and the second surface bears an additional sample and wherein the drawing step (d) liquid drawn upwardly by capillary action from the discrete aliquot also contacts the additional sample.

13. The method of claim 12 wherein the two microscope slides are of equal lengths and portions of the first and second surfaces distal from the single edge of the gap engage opposite parallel sides of a shim having a thickness of substantially the first distance.

14. The method of claim 13 wherein a first plurality of sets of microscope slides are maintained in a vertically-extending array of pairs, each pair comprising a sample-bearing microscope slide and a facing element microscope slide, with the first plurality of single edges of gaps being lower edges in a common plane, and a second plurality of discrete aliquots of liquid simultaneously contacting the lower edges.

15. The method of claim 14 wherein the second plurality of discrete aliquots are droplets in a horizontal array, each droplet being aligned with a lower edge.

16. The method of claim 15 wherein two droplets contact each lower edge.

17. The method of claim 1 further comprising the steps:
(e) removing liquid from the gap, and
(f) contacting the single lower edge of the gap with a second liquid to cause second liquid to migrate in the gap into contact with the sample.

18. The method of claim 17 wherein the removing step (e) is performed by contacting the single lower edge of the gap with an absorbent material.

19. The method of claim 1 wherein the providing step (a), maintaining step (b) and contacting step (c) are performed on a plurality of first surfaces, each bearing a thin sample.

20. The method of claim 19 wherein a plurality of discrete aliquots of liquid each contact only a single lower edge of a single gap.

21. The method of claim 20 wherein each first surface is the face of a sample-bearing microscope slide.

22. The method of claim 21 wherein each second surface is the face of a sample-bearing microscope slide, and wherein the drawing step (d) liquid drawn upwardly by capillary action from each discrete aliquot als contacts a sample on the second surface.

23. The method of claim 19 wherein the contacting step (c) the single lower edge of the gap adjacent to each first surface is simultaneously contacted by liquid.

24. The method of claim 20 wherein the plurality of discrete aliquots of liquid each contact a single lower edge of a gap simultaneously.

25. A method for treating a thin sample on a first surface with a series of treating liquids which comprises the steps:
(a) providing a thing sample on a first surface and a second surface of a facing element,
(b) drawing a first treating liquid by capillary flow in a gap between the sample-bearing first surface and the second surface to at least the position of the sample immobilized on the sample-bearing first surface,
(c) retaining the first treating liquid by capillary action in the gap in contact with the sample,
(d) removing the first treating liquid from the gap by capillary flow, and
(e) drawing a second treating liquid by capillary flow in the gap to at least the position of the sample.

26. The method of claim 25 wherein the sample-bearing first surface is the face of a microscope slide.

27. The method of claim 25 wherein the removing step (d) comprises contacting a lower edge of the gap with an absorbent material.

28. The method of claim 25 wherein the first surface and the second surface are maintained in a vertically-extending direction during the drawing steps (b) and (e) and during the removing step (d).

29. The method of claim 28 wherein the first and second surfaces are planar and wherein the first and second treating fluids are drawn from a lower edge of the gap.

30. The method of claim 29 wherein the first treating fluid withdrawn from the gap in step (d) is withdrawn through the lower edge of the gap.

31. The method of claim 30 wherein the removing step (d) comprises contacting a lower edge of the gap with an absorbent material.

32. The method of claim 25 wherein there are a first plurality of sample-bearing first surfaces, a second surface of a facing element adjacent to each first surface and a gap is formed between each first surface and the adjacent second surface, wherein the drawing step (b) first treating liquid is drawn in each gap between a first surface and a second surface, wherein the retaining step (c) first treating liquid is retained in each gap, wherein the removing step (d) first treating liquid is removed from each gap and wherein the drawing step (e) second treating liquid is drawn in each gap.

33. The method of claim 32 wherein the drawing step (b) and drawing step (e) treating fluid is simultaneously drawn into each gap.

34. A method for applying liquid to thin samples on first surface which comprises the steps:
(a) providing a first plurality of thin samples on a first plurality of vertically extending first surfaces,
(b) maintaining a second surface substantially parallel to and spaced by a first distance from each first surface, thereby providing a gap between each pair of first and second surfaces,
(c) contacting a lower edge of each gap between the vertically disposed first and second surfaces with a discrete aliquot of liquid, the aliquots of liquid being provide as a second plurality of droplets in a horizontal array, each droplet contacting a single lower edge of a single gap, and
(d) drawing liquid upwardly by capillary action within each gap from the lower edge of the gap into contact with the thin sample.

35. The method of claim 34 wherein the lower edges of each gap are contacted simultaneously with droplets.

36. The method of claim 34 wherein the first and second surfaces are each faces of vertically extending microscope slides.

* * * * *

REEXAMINATION CERTIFICATE (1506th)
United States Patent
[11] B1 4,731,335

Brigati

[45] Certificate Issued    Jul. 9, 1991

[54] METHOD FOR TREATING THIN SAMPLES ON A SURFACE EMPLOYING CAPILLARY FLOW

[75] Inventor: David J. Brigati, Dauphin, Pa.

[73] Assignee: Fisher Scientific Company, Pittsburgh, Pa.

Reexamination Request:
No. 90/002,057, Jun. 18, 1990

Reexamination Certificate for:
| | |
|---|---|
| Patent No.: | 4,731,335 |
| Issued: | Mar. 15, 1988 |
| Appl. No.: | 775,864 |
| Filed: | Sep. 13, 1985 |

[51] Int. Cl.$^5$ .............................. G01N 1/12
[52] U.S. Cl. .................. 436/180; 73/864.72; 118/421; 422/100; 427/2; 427/4; 436/63
[58] Field of Search ................ 422/100; 436/180

[56] References Cited

U.S. PATENT DOCUMENTS

| | | |
|---|---|---|
| 2,119,407 | 5/1938 | Weiskopf . |
| 2,302,830 | 11/1942 | Axelrad . |
| 2,488,535 | 11/1949 | Hamburg . |
| 2,511,730 | 6/1950 | McClain . |
| 3,358,496 | 12/1967 | Farmer . |
| 3,884,641 | 5/1975 | Kraffczyk et al. . |
| 4,022,521 | 5/1977 | Hall . |
| 4,323,536 | 4/1982 | Columbus . |
| 4,481,246 | 11/1984 | Melisz et al. . |
| 4,596,695 | 6/1986 | Cottingham . |
| 4,607,921 | 8/1986 | Miller . |
| 4,624,882 | 11/1986 | Melisz . |
| 4,647,543 | 3/1987 | Stocker . |
| 4,679,914 | 7/1987 | Rosenberg . |
| 4,761,381 | 8/1988 | Blatt et al. . |

FOREIGN PATENT DOCUMENTS

| | | |
|---|---|---|
| 0261667 | 3/1988 | European Pat. Off. . |
| 1180166 | 10/1964 | Fed. Rep. of Germany . |
| 3226407 | 1/1984 | Fed. Rep. of Germany . |
| 8624431 | 1/1987 | Fed. Rep. of Germany . |
| 819631 | 4/1981 | U.S.S.R. . |
| 2180647 | 4/1987 | United Kingdom . |

OTHER PUBLICATIONS

W. Ormanns & U. Pfeifer "A Simple Method for Incubation of Tissue Sections in Immunochemistry," Histochemistry (1981) vol. 72, pp. 315–319.

*Primary Examiner*—R. Hill

[57] ABSTRACT

Liquid is applied to a thin sample on a first surface (e.g., a specimen on a microscope slide) by maintaining a second surface parallel to the first to provide a gap therebetween and contacting an edge of the gap with a discrete aliquot of liquid. The liquid can migrate by capillary action into contact with the thin sample, preferably upward from horizontally extending linear edges of the surfaces. Liquid can also be removed by contacting the gap edges with absorbent material. Also disclosed are apparatus for holding a plurality of such surfaces in a vertically extending array and apparatus for holding a plurality of liquid droplets beneath the array. One apparatus can be moved relative to the other to contact the lower gap edges with droplets.

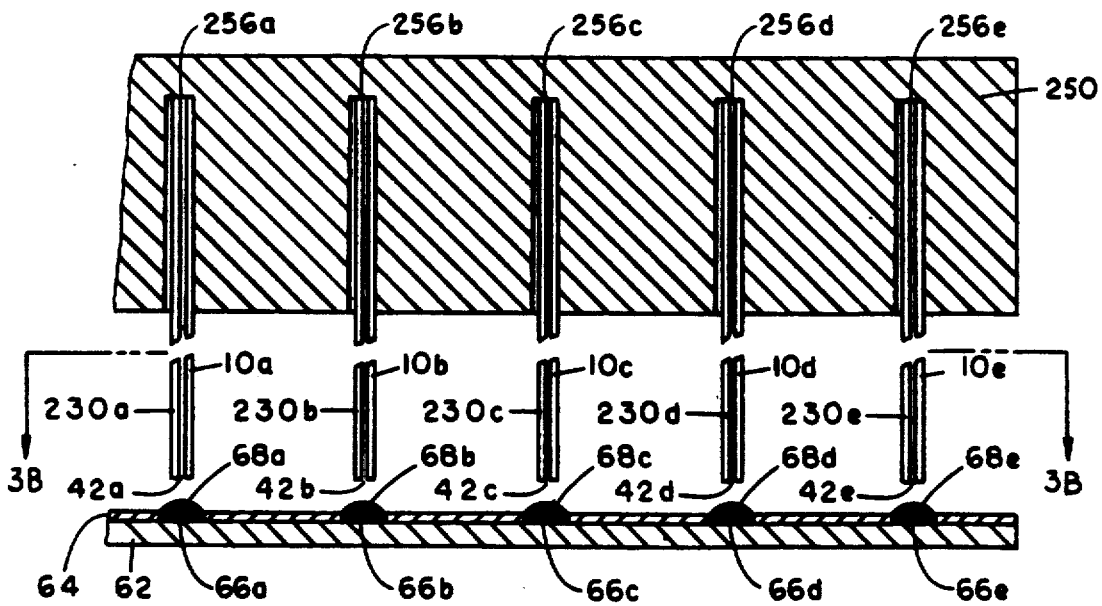

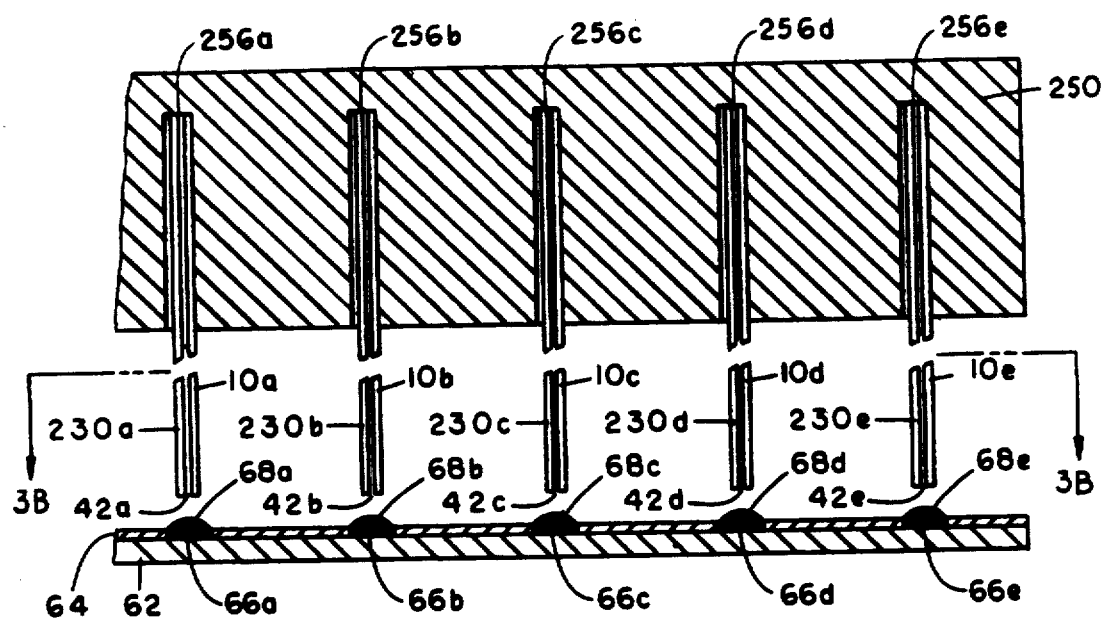

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-24 and 34-36 is confirmed.

Claims 25, 32 and 33 are determined to be patentable as amended.

Claims 26-31, dependent on an amended claim, are determined to be patentable.

25. A method for treating a thin sample on a first surface with a series of treating liquids which comprises the steps:
   (a) providing a [thing] *thin* sample on a first surface *and a second surface of a facing element, the first surface and second surface extending substantially vertically,*
   (b) drawing a first treating liquid *upwardly* by capillary flow in a gap between the sample-bearing first surface and the second surface to at least the position of the sample immobilized on the sample-bearing first surface,
   (c) retaining the first treating liquid by capillary action in the gap in contact with the sample,
   (d) removing the first treating liquid from the gap by capillary flow, and
   (e) drawing a second treating liquid *upwardly* by capillary flow in the gap to at least the position of the sample.

32. [The method of claim 25 wherein there are] *A method for treating thin samples on first surfaces with a series of treating liquids comprising the steps:*
   (a) *providing a first plurality of samples on* a first plurality of [sample-bearing] first surface, a second surface of a facing element adjacent to each first surface [and] , *with* a gap [is] *being* formed between each first surface and the adjacent second surface,
   [wherein the drawing step (b)] *(b) drawing a* first treating liquid [is drawn] *by capillary flow simultaneously* in each gap between a first surface and a second surface,
   [wherein the retaining step (c)] *(c) retaining the* first treating liquid [is retained] *by capillary action* in each gap *in contact with the sample,*
   [wherein the removing step (d)] *(d) removing* first treating liquid [is removed] from each gap *by capillary flow,* and
   [wherein the drawing step (e)] *(e) drawing a* second treating liquid is drawn] *by capillary flow simultaneously* in each gap *to at least the position of the sample.*

33. The method of claim 32 wherein the [drawing step (b) and drawing step (e)] *removing step (d) first* treating [fluid] *liquid* is simultaneously [drawn into] *removed by capillary flow from* each gap.

* * * * *